(12) United States Patent
Winkel et al.

(10) Patent No.: US 7,654,994 B2
(45) Date of Patent: Feb. 2, 2010

(54) INDICIA FOR A GARMENT WITH A DUAL FASTENING SYSTEM

(75) Inventors: Paula C. Winkel, Chilton, WI (US); Timothy J. Probst, Neenah, WI (US); Kellie M. Goodrich, Appleton, WI (US); Joseph P. Fell, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 894 days.

(21) Appl. No.: 10/953,660

(22) Filed: Sep. 28, 2004

(65) Prior Publication Data

US 2006/0069378 A1    Mar. 30, 2006

(51) Int. Cl.
  *A61F 13/15*   (2006.01)
  *A61F 13/20*   (2006.01)
(52) U.S. Cl. .................. 604/386; 604/389; 604/391
(58) Field of Classification Search ............... 604/386, 604/389, 391
  See application file for complete search history.

(56) References Cited

U.S. PATENT DOCUMENTS

| | | | |
|---|---|---|---|
| 3,961,112 A | 6/1976 | Genevitz et al. | |
| 4,076,663 A | 2/1978 | Masuda et al. | |
| 4,286,082 A | 8/1981 | Tsubakimoto et al. | |
| 4,334,530 A | 6/1982 | Hassell | |
| 4,662,875 A | 5/1987 | Hirotsu et al. | |
| 4,663,220 A | 5/1987 | Wisneski et al. | |
| 4,699,622 A | 10/1987 | Toussant et al. | |
| 4,798,603 A | 1/1989 | Meyer et al. | |
| 4,883,480 A | 11/1989 | Huffman et al. | |
| 4,988,346 A | 1/1991 | Pfefferkorn | |
| 5,019,070 A | 5/1991 | Ruben | |
| 5,114,781 A | 5/1992 | Morman | |
| 5,116,662 A | 5/1992 | Morman | |
| 5,133,707 A | 7/1992 | Rogers et al. | |
| 5,151,092 A | 9/1992 | Buell et al. | |
| 5,226,992 A | 7/1993 | Morman | |
| 5,383,871 A | 1/1995 | Carlin et al. | |
| 5,454,803 A | 10/1995 | Sageser et al. | |
| 5,531,731 A | 7/1996 | Brusky | |
| 5,560,798 A | 10/1996 | Brusky | |
| H1674 H | 8/1997 | Ames et al. | |
| 5,685,873 A | 11/1997 | Bruemmer | |
| 5,695,488 A | 12/1997 | Sosalla | |
| 5,695,868 A | 12/1997 | Mccormack | |
| 5,776,123 A * | 7/1998 | Goerg et al. | ................. 604/391 |

(Continued)

FOREIGN PATENT DOCUMENTS

EP        0 444 353 A1    9/1991

(Continued)

*Primary Examiner*—Melanie J Hand
(74) *Attorney, Agent, or Firm*—Bryan R. Rosiejka

(57) ABSTRACT

A disposable garment including a dual fastening system. The dual fastening system includes at least two first fasteners and at least two second fasteners, at least a portion of each second fastener being located in the front waist region and situated inboard from each longitudinal side edge of the front waist region, each second fastener being configured to engage at least a portion of the bodyfacing surface. Additionally, the bodyfacing surface comprises indicia in the rear waist region guiding a user fitting the disposable garment regarding the positioning of the second fasteners.

26 Claims, 4 Drawing Sheets

U.S. PATENT DOCUMENTS

| | | | |
|---|---|---|---|
| 5,788,685 A | 8/1998 | Ronnberg et al. | |
| 5,843,056 A | 12/1998 | Good et al. | |
| 5,883,028 A | 3/1999 | Morman et al. | |
| 5,897,546 A * | 4/1999 | Kido et al. | 604/391 |
| 6,045,543 A * | 4/2000 | Pozniak et al. | 604/385.01 |
| 6,142,983 A | 11/2000 | Suprise et al. | |
| 6,159,596 A | 12/2000 | Calhoun et al. | |
| 6,174,303 B1 | 1/2001 | Suprise et al. | |
| 6,352,528 B1 * | 3/2002 | Weber et al. | 604/385.03 |
| 6,613,032 B2 | 9/2003 | Ronnberg et al. | |
| 6,733,483 B2 | 5/2004 | Raufman et al. | |
| 6,945,968 B2 | 9/2005 | Svensson et al. | |
| 2005/0148976 A1 | 7/2005 | Van Gompel et al. | |
| 2005/0148987 A1 | 7/2005 | Van Gompel et al. | |

FOREIGN PATENT DOCUMENTS

| | | |
|---|---|---|
| EP | 0 217 032 B1 | 2/1992 |
| EP | 0 682 928 A1 | 11/1995 |
| EP | 0 539 703 B1 | 3/1997 |
| EP | 0 941 728 A2 | 9/1999 |
| EP | 1 038 511 A1 | 9/2000 |
| EP | 0 756 855 B1 | 11/2000 |
| GB | 2 267 024 A | 11/1993 |
| WO | WO 95/08313 A2 | 3/1995 |
| WO | WO 99/22688 A1 | 5/1999 |
| WO | WO 00/35401 A1 | 6/2000 |
| WO | WO 01/21126 A1 | 3/2001 |
| WO | WO 02/41819 A1 | 5/2002 |
| WO | WO 02/49568 A1 | 6/2002 |
| WO | WO 2003/034966 A1 | 5/2003 |

* cited by examiner

INDICIA FOR A GARMENT WITH A DUAL FASTENING SYSTEM

BACKGROUND OF THE INVENTION

In general, personal care articles should comfortably fit the body of a wearer. Personal care articles may have fastening tabs located at the rear of the personal care article that extend outwardly and secure to a front portion of the article. For the personal care article to be effective, the fastening tabs should be properly placed on the front portion of the personal care article. Additionally, personal care articles may have second fastening tabs located at the front of the personal care article that extend outwardly and secure to a rear portion of the article. For the personal care article to be effective, these fastening tabs should be properly placed on the rear portion of the personal care article.

To achieve the optimal combination of comfortable fit, absorbency and leakage protection, the caregiver is encouraged to don the personal care article on the wearer so that the front and rear waist regions are substantially aligned with each other. For some diaper structures, the optimal properties may be achieved by perfect alignment of the front and rear waist regions. For many diaper structures, the optimal properties are achieved by aligning the waistband regions so that the front waist edge is slightly below the back waist edge relative to a standing wearer. For the caregiver, it has often been difficult to place the diaper structure under the baby or other wearer and fasten it to achieve optimal alignment, without multiple attempts. Often, the caregiver fastens the diaper structure on the wearer and then discovers that the waistband regions are not optimally aligned. The caregiver must then unfasten the diaper structure, reposition it, and fasten it again until optimal alignment is achieved.

Similarly, the caregiver is encouraged to don the diaper structure on the wearer so that the center of the back waistband and the center of the front waistband align with the center of the wearer's back and stomach. The encouraged side-to-side alignment keeps the leg elastics equally tight on the wearer's legs, thus preventing irritation on one side and leakage on the other side. More particularly, if the diaper is cocked to one side or the other side, the size of the leg holes is disproportionate. The leg elastics then apply unequal tension, resulting in one side that is tight and the other side that is loose. The donning process may be complicated with the addition of multiple fasteners.

Therefore, it is important to ensure that the front fastening tabs are secured on the rear portion of the personal care article properly.

SUMMARY

In response to the foregoing need, the present inventors undertook intensive research and development efforts that resulted in the discovery of an improved dual fastening system with placement aids. One version of the disposable garment of the present invention includes opposed longitudinal side edges, opposed lateral end edges, a front waist region, a rear waist region and a crotch region which extends between and connects the front waist region and the rear waist region. The disposable garment also includes a bodyfacing surface, a garment facing surface, and a dual fastening system. The dual fastening system includes at least two first fasteners located on first fastener tabs, at least a portion of each first fastener being situated inboard from each longitudinal side edge of the rear waist region, each first fastener being configured to engage at least a portion of the garment facing surface. The dual fastening system also includes at least two second fasteners located on second fastener tabs, at least a portion of each second fastener being located in the front waist region and situated inboard from each longitudinal side edge of the front waist region, each second fastener being configured to engage at least a portion of the bodyfacing surface. Additionally, the bodyfacing surface comprises indicia in the rear waist region guiding a user fitting the disposable garment regarding the positioning of the second fasteners.

Another version of disposable garment of the present invention includes opposed longitudinal side edges, opposed lateral end edges, a front waist region, a rear waist region and a crotch region which extends between and connects the front waist region and the rear waist region. The disposable garment also includes a bodyfacing surface, a garment facing surface and a dual fastening system. The dual fastening system includes at least two first fasteners located on first fastener tabs, at least a portion of each first fastener being situated inboard from each longitudinal side edge of the rear waist region, each first fastener being configured to engage at least a portion of the garment facing surface. The dual fastening system also includes at least two second fasteners located on second fastener tabs, at least a portion of each second fastener being located in the front waist region and situated inboard from each longitudinal side edge of the front waist region, each second fastener being configured to engage at least a portion of the bodyfacing surface. Additionally, the bodyfacing surface comprises first indicia in the rear waist region guiding a user fitting the disposable garment regarding the positioning of the second fasteners and the garment facing surface comprises indicia in the front waist region guiding a user fitting the disposable garment regarding the positioning of the first fasteners.

Still another version of the disposable garment of the present invention includes opposed longitudinal side edges, opposed lateral end edges, a front waist region, a rear waist region and a crotch region which extends between and connects the front waist region and the rear waist region, the front waist region having a width extending between opposed longitudinal side edges and the rear waist region having a width extending between opposed longitudinal side edges. The disposable absorbent article includes an outer cover; a bodyside liner, an absorbent core disposed between the bodyside liner and the outer cover and a dual fastening system. The dual fastening system includes at least two first fasteners located on first fastener tabs, at least a portion of each first fastener being situated inboard from each longitudinal side edge of the rear waist region, each first fastener being configured to engage at least a portion of the garment facing surface. The dual fastening system also includes at least two second fasteners located on second fastener tabs, at least a portion of each second fastener being located in the front waist region and situated inboard from each longitudinal side edge of the front waist region, each second fastener being configured to engage at least a portion of the bodyfacing surface. Additionally the bodyfacing surface comprises first indicia in the rear waist region guiding a user fitting the disposable absorbent article regarding the positioning of the second fasteners and the garment facing surface comprises indicia in the front waist region guiding a user fitting the disposable garment regarding the positioning of the first fasteners, and the first fastener and the second fastener are hook material.

DRAWINGS

The foregoing and other features and aspects of the present invention and the manner of attaining them will become more apparent, and the invention itself will be better understood by reference to the following description, appended claims and accompanying drawings, where:

DESCRIPTION

Figure 1:
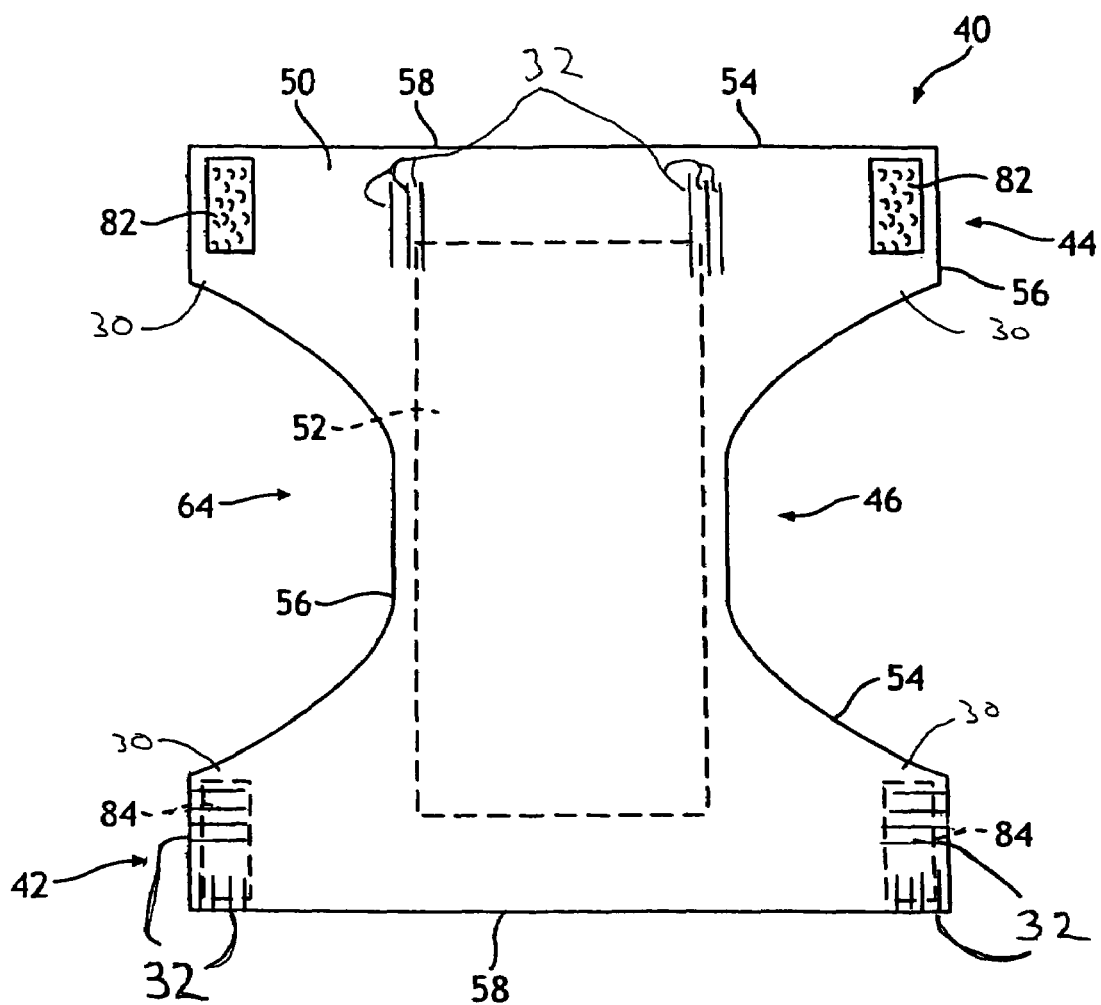
FIG. 1 illustrates a plan view of the bodyfacing surface of a representative disposable absorbent article incorporating a version of the improved dual fastening system.

The present disclosure of the invention will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "prefastened" refers to a condition wherein the absorbent article has a fastening feature, which is engaged or fastened prior to use by the wearer. For example, the fastening feature of the absorbent article may be engaged or fastened during the manufacturing process.

The present invention is directed to disposable garments having an improved fastening system. Additionally, the present invention is directed to a garment having a unique combination of features that provide previously unrecognized and unexpected benefits. This detailed description of the present invention will include a description of a representative disposable garment including the various components of such garments. The description of the representative disposable garment will also include a description of many features encompassed by the present invention.

Representative Disposable Garment

The present invention concerns an improved dual fastening system for use with disposable garments. The disposable garments are adapted to be worn adjacent to the body of a wearer, that is, a disposable garment that is similar to a disposable diaper. It is understood that the features of the present invention are equally adaptable for other types of disposable garments such as adult incontinence garments, training pants, disposable swim pants and feminine hygiene garments.

As used herein, the term "disposable" refers to garments which are intended to be discarded after a limited use and which are not intended to be laundered or otherwise restored for reuse. The disposable garments of the present invention will be described in terms of a disposable diaper which is adapted to be worn by infants about the lower torso.

With regard to the designated surfaces of a disposable absorbent article and its components, the various upper or bodyfacing surfaces are configured to face toward the body of the wearer when the disposable absorbent article is worn by the wearer for ordinary use. The various opposing, lower or garment facing surfaces are configured to face away from the wearer's body when the disposable absorbent article is worn by the wearer.

As used herein, reference to two materials or elements being "joined" is intended to refer to the situation wherein the two materials or elements are directly joined to one another or where they are indirectly joined to one another or where they are indirectly joined to an intermediate element. Similarly, methods of joining two materials or elements include forming the elements or materials integrally, or attaching the elements together such as through the use of adhesive bonds, sonic bonds, thermal bonds, pinning, stitching, or a variety of other attachment techniques known in the art, as well as combinations thereof.

Stretchable materials may include materials that are extensible and materials that are elastomeric. Extensible materials typically have lower capacities to retract to their original lengths after stretching, while elastomeric materials typically have a greater range of stretch and come close to completely retracting to their original lengths. It should be noted that the elongation, extension or permanent deformation properties of an extensible material are determined when the material is dry. Additionally, the percentage of elongations extension or permanent deformation can be determined in accordance with the following formula:

$$100*[(L-Lo)/(Lo)]$$

where:

L=elongated length; and

Lo=initial length.

Figure 2:
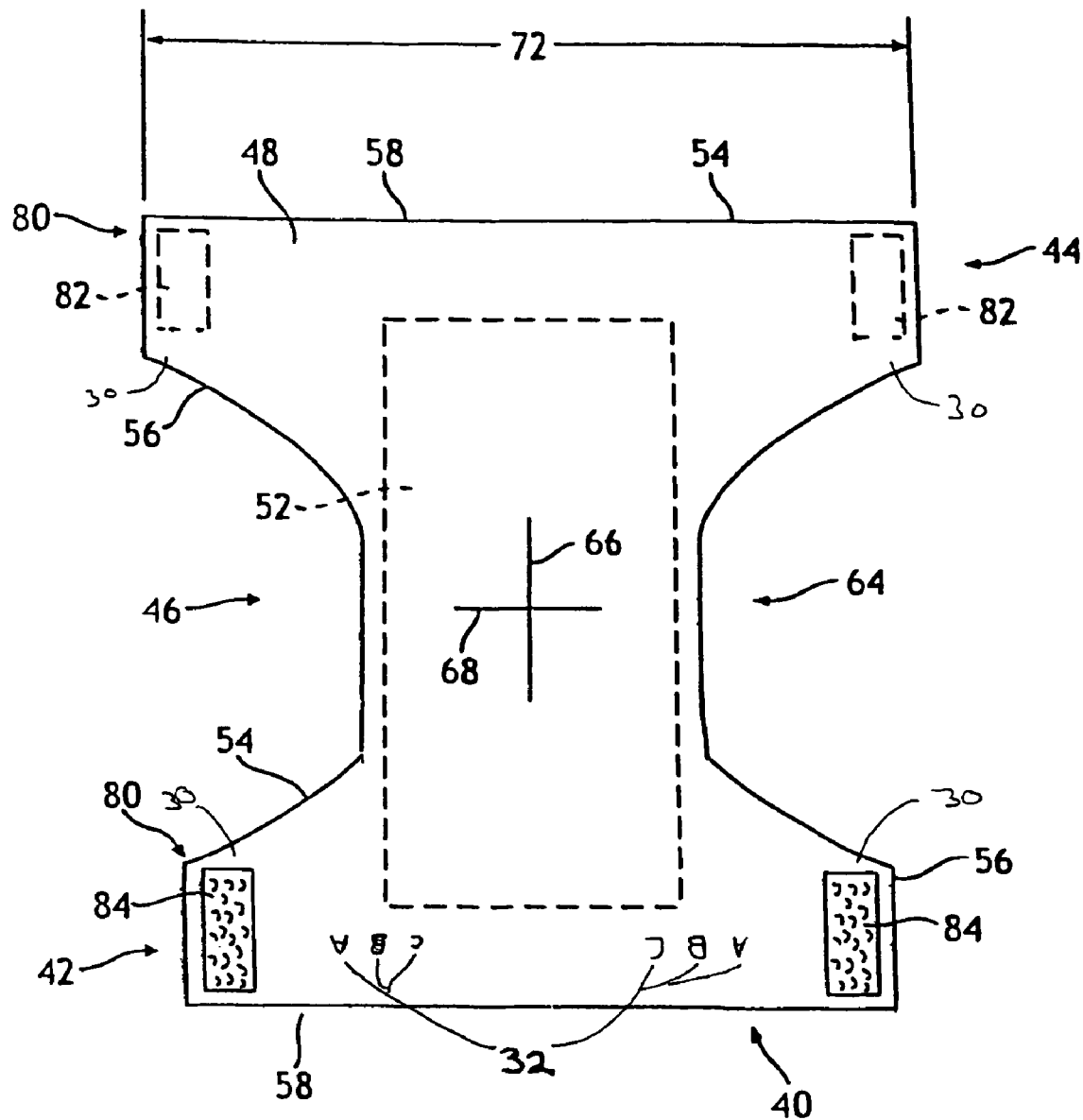
FIG. 2 illustrates a plan view of the garment facing surface of a representative disposable absorbent article incorporating a version of the improved dual fastening system.
Figure 3:
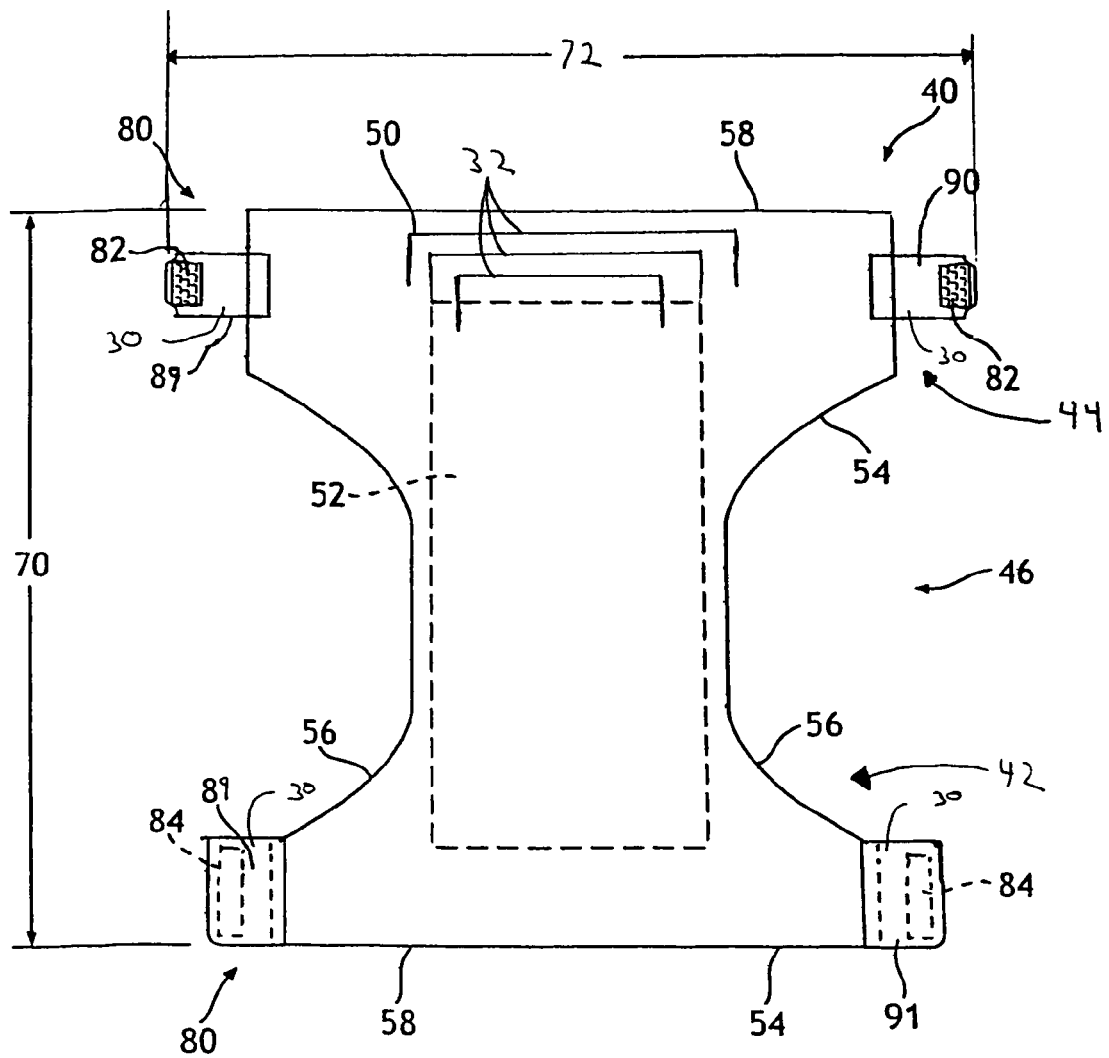
FIG. 3 illustrates a plan view of the bodyfacing surface of a representative disposable absorbent article incorporating a version of the improved dual fastening system.

FIGS. 1-3 representatively illustrate examples of a disposable garment, in this instance a diaper (as generally indicated at 40). Referring to FIGS. 1-3, the diaper (40) defines a front waist region (42), a rear waist region (44) and a crotch region (46) which extends between and connects the front (42) and rear (44) waist regions. The front waist region (42) comprises the portion of the diaper (40) which, when worn, is positioned on the front of the wearer, while the rear waist region (44) comprises the portion of the diaper which, when worn, is positioned on the back of the wearer. The crotch region (46) of the diaper (40) comprises the portion of the diaper which, when worn, is positioned between the legs of the wearer and covers the lower torso of the wearer.

The diaper (40) also includes an outer cover (48), a bodyside liner (50), and an absorbent core (52) situated between the outer cover (48) and the liner (50). The outer edges of the diaper (40) define a periphery (54) with laterally opposed, longitudinally extending side edges (56) and longitudinally opposed, laterally extending end edges (58). The diaper (40) may also include a system of elastomeric gathering members, such as leg elastics and waist elastics (not illustrated). The longitudinal side edges (56) define leg openings (64) for the diaper (40), and optionally are curvilinear and contoured. The lateral end edges (58) are illustrated as straight, but optionally, may be curvilinear. The diaper (40) additionally has a longitudinal centerline (66) and a lateral centerline (68). The diaper (40) may also include additional components to assist in the acquisition, distribution and storage of bodily waste.

For example, the diaper (40) may include a transport layer, such as described in U.S. Pat. No. 4,798,603, issued to Meyer et al., or a surge management layer, such as described in European Patent Application Publication No. 0 539 703, published May 5, 1993.

As used herein, the term "inboard" is intended to refer to the direction from an edge toward a respective centerline. The term "outboard" is intended to refer to a direction away from a respective centerline.

The diaper (40) generally defines a longitudinally extending length dimension (70), and a laterally extending width dimension (72) (as representatively illustrated in FIGS. 2 and 3). The diaper may have any desired shape, such as rectangular, 1-shaped, a generally hourglass shape, or a T-shape.

The outer cover (48) and the liner (50) may be generally coextensive (e.g., FIG. 2), or optionally, may be non-coextensive. Either or both of the outer cover (48) and the liner (50) may have length and width dimensions which are generally larger than those of the absorbent core (52) and extend beyond the corresponding dimensions of the absorbent core (52) to provide longitudinal side edges (56) and lateral end edges (58) which may be connected or otherwise associated together in an operable manner.

The outer cover (48) can be composed of various materials and is suitably liquid impermeable. Desirably the outer cover (48) is made of a stretchable material. In a particular aspect, the outer cover (48) is made of an elastomeric material. Suitable elastomeric materials are stretchable in one or more directions. Elastomeric materials may include cast or blown films, foams, or meltblown fabrics composed of polyethylene, polypropylene, or polyolefin copolymers, as well as combinations thereof. The elastomeric materials may include PEBAX elastomer (available from AtoChem located in Philadelphia, Pa.), HYTREL elastomeric polyester (available from E.I. DuPont de Nemours of Wilmington, Del.), KRATON elastomer (available from Kraton Polymers of Houston, Tex.), or strands of LYCRA elastomer (available from E.I. DuPont de Nemours of Wilmington, Del.), or the like, as well as combinations thereof. The outer cover (48) may include materials that have elastomeric properties through a mechanical process, printing process, heating process, or chemical treatment. For example, such materials may be apertured, creped, neck-stretched, heat activated, embossed, and micro-strained; and may be in the form of films, webs, and laminates.

In particular aspects, the outer cover (48) may include a 0.4 ounces per square yard (osy) (13.6 grams per square meter (gsm)) basis weight layer of G2760 KRATON elastomer strands adhesively laminated with a 0.3 gsm layer of adhesive between two facings. Each facing can be composed of a thermal point bonded bicomponent spunbond non-woven fibrous web having a 0.7 osy (23.7 gsm) basis weight. The adhesive is an adhesive which is supplied by AtoFindley Adhesive, a business having offices in Wauwatosa, Wis., and designated as H2525A, and the elastomer strands are placed and distributed to provide approximately 12 strands of KRATON elastomer per inch (2.54 cm) of lateral width of the outer cover (48).

Materials suitable for a biaxially stretchable outer cover (48) include biaxially stretchable materials and biaxially elastic stretchable materials. One example of a suitable outer cover material can include a 0.3 osy (10 gsm) polypropylene spunbond that is necked 60% in the lateral direction and creped 60% in the longitudinal direction, laminated with 3 grams per square meter (gsm) AtoFindley Adhesives H2525A styrene-isoprene-styrene based adhesive to 8 gsm PEBAX 2533 film with 20% $TiO_2$ concentrate. The outer cover (48) can suitably be stretched, laterally and/or longitudinally, by at least 30% (to at least 130% of an initial (unstretched) width and/or length of the outer cover (48)). More suitably, the outer cover (48) can be stretched laterally and/or longitudinally, by at least 50% (to at least 150% of the unstretched width or length of the outer cover (48)). Even more suitably, the outer cover (48) can be stretched, laterally and/or longitudinally, by at least 100% (to at least 200% of the unstretched width or length of the outer cover (48)). Tension force in the outer cover (48) at 50% extension is suitably between 50 and 1000 grams, more suitably between 100 and 600 grams, as measured on a 3 inch (7.62 cm) wide piece of the outer cover material.

Another example of a suitable material for a biaxially stretchable outer cover (48) is a breathable elastic film/nonwoven laminate, described in U.S. Pat. No. 5,883,028, issued to Morman et al, incorporated herein by reference to the extent that it is consistent (i.e., not in conflict) herewith. Examples of materials having two-way stretchability and retractability are disclosed in U.S. Pat. No. 5,116,662, issued to Morman, and U.S. Pat. No. 5,114,781, issued to Morman, both of which are hereby incorporated herein by reference to the extent that each is consistent (i.e., not in conflict) herewith. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

In an alternative aspect, the outer cover (48) is made of an extensible material. Extensible materials suitable for use as an outer cover (48) can provide an elongation of at least 10; alternatively, at least 20; alternatively, at least 30; or, alternatively, at least 40% when subjected to a tensile force of 30 gmf per inch (per 2.54 cm). Material suitable for use as an outer cover (48) can also provide a substantially permanent deformation of at least 10; alternatively, at least 15; alternatively, at least 20; alternatively, at least 25; or, alternatively, at least 30% when subjected to a tensile force of 50 gmf per inch (per 2.54 cm) and then allowed to relax, after removal of the tensile force, for a period of 1 minute. It should be readily appreciated that the described removal of the applied force results in a zero applied tensile stress and a zero applied tensile force.

The outer cover (48) can be composed of various materials and is suitably liquid impermeable. If extensible, for example, the outer cover (48) can be composed of a necked fabric, a creped fabric, a crimped fiber fabric, an extendable fiber fabric, a bonded-carded fabric, a micro-pleated fabric, polymer films or the like, as well as combinations thereof.

The fabrics may be knit, woven or non-woven materials, such as spunbond fabrics. In a particular aspect, the outer cover (48) can be composed of an extensible laminate of two or more layers. For example, the outer cover (48) may be a necked laminate formed from at least one neckable fabric laminated to at least one extendable film material wherein the necked laminate is extensible in at least one direction. The outer cover material (48), if extensible, may otherwise be a laminate formed from at least one necked fabric laminated to at least one extendable film material. In such a configuration, the laminate need not be necked. For purposes of the present description, the term "nonwoven web" refers to a web of fibrous material that is formed without the aid of a textile weaving or knitting process.

The term "fabrics" is used to refer to woven, knitted and nonwoven fibrous webs. An example of an extensible material suitable for use as an outer cover (48) is a 60% necked, polypropylene spunbond having a basis weight of about 1.2 osy (41 gsm).

The liner (50) suitably presents a bodyfacing surface which is compliant, soft feeling, and non-irritating to the wearer's skin. Further, the liner (50) may be less hydrophilic than the absorbent core (52), to present a relatively dry surface to the wearer, and is sufficiently porous to be liquid permeable, permitting liquid to readily penetrate through its thickness. A suitable liner (50) may be manufactured from a wide selection of web materials, such as porous foams, reticulated foams, apertured plastic films, natural fibers, synthetic fibers (for example, polyester or polypropylene fibers), or a combination of natural and synthetic fibers. The liner (50) is suitably employed to help isolate the wearer's skin from liquids held in the absorbent core (50).

Desirably the liner (50) is made of a stretchable material. In a particular aspect, the liner (50) is made of an elastomeric material. Suitable elastomeric materials are stretchable in one or more directions. Suitable elastomeric materials for construction of the liner (50) can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from B.F. Goodrich and Company of Cleveland, Ohio), or PEBAX elastomers.

As an additional example, in one aspect the liner (50) suitably includes a non-woven, spunbond polypropylene fabric composed of about 2 to 3 denier fibers formed into a web having a basis weight of about 12 gsm which is necked approximately 60%. Strands of about 9 gsm KRATON G2760 elastomer material placed eight strands per inch (2.54 cm) are adhered to the necked spunbond material. The fabric is surface treated with an operative amount of surfactant, such as about 0.6 percent AHCOVEL Base N62 surfactant, available from ICI Americas, a business having offices in Wilmington, Del. The surfactant can be applied by any conventional means, such as spraying, printing, brush coating or the like. Other suitable materials may be extensible biaxially stretchable materials, such as a neck stretched/creped spunbond.

In an alternative aspect, the liner (50) is made of an extensible material. Extensible liner materials (50) can provide an elongation of at least 50% when subjected to a tensile force of 10 gmf per inch (per 2.54 cm). Extensible materials suitable for use as a liner (50) can also provide a substantially permanent deformation of at least 10% when subjected to a tensile force of 50 gmf per inch (per 2.54 cm) and then allowed to relax, after removal of the tensile force, for a period of 1 minute. It should be readily appreciated that the described removal of the applied force results in a zero applied tensile stress and a zero applied tensile force.

A suitable extensible liner (50) may be manufactured from a wide range of materials including, but not limited to knit, woven and nonwoven materials, apertured formed thermoplastic films, apertured plastic films, hydro-formed films, porous foams, reticulated foams, reticulated thermoplastic films, and thermoplastic scrims. Suitable woven and nonwoven materials can include natural fibers (e.g., wood or cotton fibers), synthetic or modified natural fibers (e.g., polymeric fibers, such as polyester, polypropylene fibers, and polyethylene, or polyvinylalcohol, starch base resins, polyurethanes, cellulose esters, nylon, and rayon fibers), or a combination of natural and synthetic fibers. When the extensible liner material (50) includes a nonwoven web, the web may be spunbonded, carded, wet-laid, meltblown, hydroentangled, combinations of the above, or the like. An example of a suitable extensible liner (50) is a 50% necked, polypropylene spunbond having a basis weight of about 0.5 osy.

As previously mentioned, the liner (50) may be treated with a surfactant. This can be accomplished by a variety of techniques known to those skilled in the art. Treating the liner (50) with a surfactant generally renders the liner (50) more hydrophilic. This typically results in liquid penetrating the liner (50) faster than if it were not treated.

The absorbent core (52) may include a matrix of hydrophilic fibers, such as a web of cellulosic fluff, mixed with particles of a high-absorbency material commonly known as superabsorbent material. In a particular version, the absorbent core (52) includes a mixture of superabsorbent hydrogel-forming particles and wood pulp fluff. The wood pulp fluff may be exchanged with synthetic polymeric, meltblown fibers or with a combination of meltblown fibers and natural fibers. The superabsorbent particles may be substantially homogeneously mixed with the hydrophilic fibers or may be non-uniformly mixed.

The absorbent core (52) may have any of a number of shapes. For example, the absorbent core (52) may be rectangular, 1-shaped or T-shaped. It is often desired that the absorbent core (52) be narrower in the crotch portion than the rear or front portion(s).

The high-absorbency material can be selected from natural, synthetic and modified natural polymers and materials. The high-absorbency materials can be inorganic materials, such as silica gels, or organic compounds, such as crosslinked polymers. The term "crosslinked", refers to any means for effectively rendering normally water-soluble materials substantially water insoluble, but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful. Processes for preparing synthetic, absorbent gelling polymers are disclosed in U.S. Pat. No. 4,076,663, issued to Masuda et al., and U.S. Pat. No. 4,286,082, issued to Tsubakimoto et al.

The high-absorbency material may be in a variety of geometric forms. It is desired that the high-absorbency material be in the form of discrete particles. However, the high-absorbency material may also be in the form of fibers, flakes, rods, spheres, needles, or the like. Often, the high-absorbency material is present in the absorbent core (52) in an amount of from about 5 to about 100 weight percent based on total weight of the absorbent core (52).

Referring again to FIGS. 1-3, illustrated are versions of a diaper (40) in its generally flat-out, uncontracted state (i.e., with all elastic induced gathering and contraction removed). The diaper (40) includes a liner (50) and an outer cover (48) which are coextensive and have length and width dimensions generally larger than those of an absorbent core (52). The liner (50) is associated with and superposed on the outer cover (48) to thereby form the periphery (54) of the diaper (40). The periphery (54) defines an outer perimeter or edge(s) of the diaper (40). The periphery (54) generally includes longitudinal side edges (56) and lateral end edges (58).

The disposable absorbent articles described herein also include a dual fastening system (80) for securing the absorbent article about the waist of the wearer. The illustrated versions of the diaper (40) include such a dual fastening system (80). Specifically, the dual fastening system includes at least two first fasteners (82) and at least two second fasteners (84). The first fasteners (82) are situated in the rear waist region (44) of the diaper (40), and located inboard each longitudinal side edge (56). The first fasteners (82) engage the outer cover (48) of the front waist region (42) of the diaper (40) for holding the diaper on the wearer. Desirably, the first fasteners (82) are releasably engageable directly with the garment facing surface of the outer cover (48). Alternatively, the diaper (40) may include a fastening panel (not illustrated) situated in the front waist region (42) of the garment facing surface of the outer cover (48). In this configuration, the fastening panel forms a portion of the garment facing surface of the garment. In such a configuration, the first fasteners (82) are releasably engageable with the fastening panel to maintain the diaper (40) about the waist of the wearer. As representatively illustrated in FIGS. 1 and 3, the first fasteners (82) may be hook type fasteners and the outer cover (48) or fastening panel may be configured to function as a complimentary loop type fastener. Desirably, the first fasteners (82) are hook type fasteners which are releasably engageable with the outer cover (48). Such an arrangement provides the ability to vary the size of the waist opening in very small increments over a wide range to fit the waist of the wearer. The first fasteners (82) may have a variety of shapes and sizes which provide the desired fastening of the diaper (40) about the waist of the wearer.

The dual fastening system (80) of the present invention further includes at least two second fasteners (84) to provide improved securement of the diaper (40) about the waist of the wearer. For example, as representatively illustrated in FIGS. 1-3, the diaper (40) may include at least two second fasteners (84) situated in the front waist region (42) of the diaper, and located adjacent each longitudinal side edge (56). The second fasteners (84) are configured to encircle the hips of the wearer and engage the bodyfacing surface of the liner (50) in the rear waist region (44) of the diaper (40). Suitably, as representatively illustrated in FIG. 2, the second fasteners (84) are hook type fasteners which are releasably engageable directly with the bodyfacing surface of the liner (50). Alternatively, the diaper (40) may include one or more fastening panels (not illustrated) on the bodyfacing surface of the rear waist region (44) to which the second fasteners (84) are releasably engageable.

The dual fastening system (80) may be presented to a user in a flat configuration, such that the user may don the garment without removal of clothes. Alternatively, the dual fastening system (80) may be presented to a user in a prefastened configuration, such that the user may don the garment as one would don underpants.

The term fastening tab as used in the present application refers to the laterally outward portions of the front or rear waist region (42, 44). The dual fastening system (80) includes fastening tabs (30). Fastening tabs (30) may be secured to the bodyfacing surface by ultrasonic bonding at opposing sides of front and rear waist regions (42, 44) of the disposable garment (as shown in FIG. 3). Each fastening tab (30) includes a bodyfacing surface and a garment facing surface. Each fastening tab (30) further includes first (82) or second (84) fasteners attached to the fastening tabs on the bodyfacing or garment facing surface.

While ultrasonic bonding is disclosed as a method for mounting fastening tabs (30), other well known methods are contemplated. For example, curing adhesives, stitching, and pressure sensitive adhesives, are all potential mechanisms for suitably and permanently securing the inboard ends of fastening tabs (30). Fastening tabs (30) may be secured to the bodyfacing surface, alternatively, fastening tabs (30) may be secured to the garment facing surface, alternatively, fastening tabs (30) may be secured between the garment facing and bodyfacing surfaces.

Fastening tabs (30) may be formed as an integral part of the garment facing surface and/or the bodyfacing surface (as shown in FIGS. 1 and 2). Such an arrangement reduces the amount of elements needed to form the garment.

Fastening tab (30) may includes a tab substrate preferably comprising a non-woven material, such as spunbond-meltblown-spunbond material (SMS). Spunbond-meltblown-spunbond material comprises a layer of meltblown material disposed between and in surface-to-surface relationship with the spunbond layers.

Other materials having suitable characteristics can be substituted for the above described tab substrates for fastening tab (30). Furthermore, extensible materials can be utilized for the tab substrate.

Figure 4:
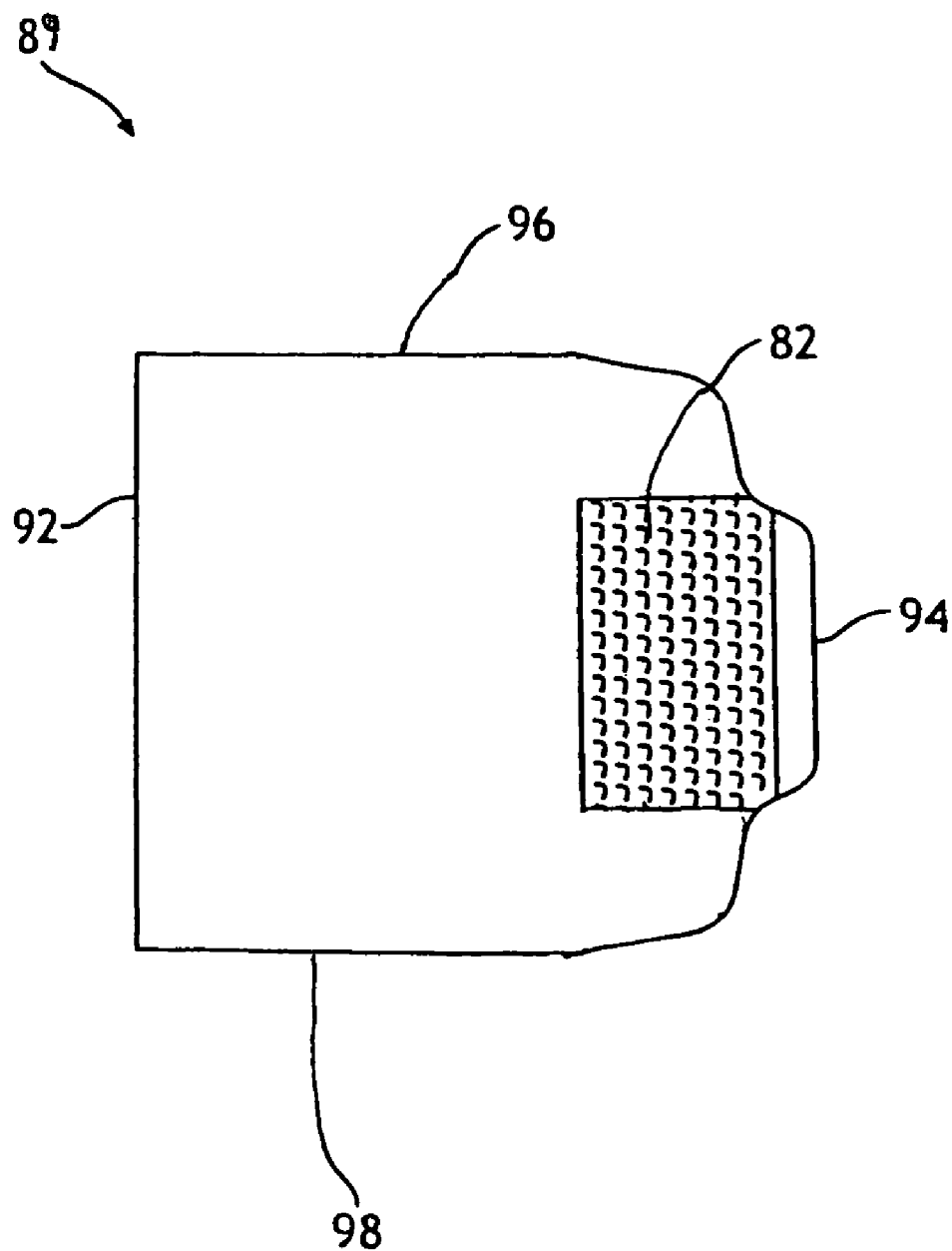
FIG. 4 illustrates a version of an ear suitable for incorporation into a version of the improved dual fastening system.

An alternative dual fastening system (80) may include one or more ears (89). As illustrated in FIGS. 3 and 4, each ear (89) includes a proximal edge (92), an opposed distal edge (94), a first connecting edge (96), and a second connecting edge (98). As used herein, the proximal edge (92) is that edge of the ear (89) located nearest to the longitudinal centerline (66). The distal edge (94) is that edge of the ear (89) which is opposite the proximal edge (92). The first (96) and second (98) connecting edges connect the proximal edge (92) and the distal edge (94) thereby defining a body of material which at least partially defines an ear (89). The ear (89) may be made of a variety of materials including those that are extensible, non extensible, elastomeric and/or non-elastomeric. Desirably, the ear (89) is made of a non-elastomeric material.

The diaper (40) illustrated in FIG. 3 includes a version of the alternative dual fastening system (80) described herein. Specifically, the dual fastening system (80) includes at least two first fasteners (82) and at least two second fasteners (84). Typically, the first fasteners (82) are located inboard of a distal edge (94) on a bodyfacing surface of a first ear (90). At least a portion of the proximal edge (92) of the first ear (90) is joined to the rear waist region (44) of the diaper (40), with the distal edge (94) of the ear extending outboard from the longitudinal centerline (66) and forming a portion of the side edge (56) of the diaper. Desirably, the first fasteners (82) are releasably engageable directly with the garment facing surface of the outer cover (48). Alternatively, the diaper (40) may include a fastening panel (not illustrated) situated in the front waist region (42) of the garment facing surface of the outer cover (48). In such a configuration, the first fasteners (82) are releasably engageable with the fastening panel to maintain the diaper (40) about the waist of the wearer.

The dual fastening system of this alternate version also includes a pair of second fasteners (84). Specifically, the second fasteners (84) are located inboard of a distal edge (94) on a garment facing surface of a second ear (91). At least a portion of the proximal edge (92) of the second ear (91) is joined to the front waist region (42) of the diaper (40), with the distal edge (94) of the ear extending outboard from the longitudinal centerline (66) and forming a portion of the side edge (56) of the diaper. Desirably, the second fasteners (84) are hook type fasteners which are releasably engageable directly with the bodyfacing surface of the liner (50). Alternatively, the diaper (40) may include one or more fastening panels (not illustrated) on the bodyfacing surface of the rear waist region (44) to which the second fasteners (84) are releasably engageable.

Suitable fasteners are well known to those of skill in the art and can include adhesive tape tab fasteners, hook and loop fasteners, mushroom fasteners, snaps, pin, belts and the like, and combinations thereof. For example, as representatively illustrated in FIGS. 1 and 3, the first fasteners (82) may be hook type fasteners and the outer cover (48) or fastening panel (not illustrated) may be configured to function as a complimentary loop type fastener. Desirably, the first fasteners (82) are hook type fasteners which are releasably engageable with at least a portion of an outer cover (48). The second fasteners (84) may also be hook type fasteners (as representatively illustrated in FIG. 2) and the liner (50) or fastening panel (not illustrated) may be configured to function as a complimentary loop type fastener. Desirably, the second fasteners (84) are hook type fasteners which are releasably engageable with at least a portion of a liner (50). Such an arrangement provides the ability to vary the size of the waist opening in very small increments over a wide range to fit the waist of the wearer. The first (82) and second (84) fasteners may have a variety of shapes and sizes which provide the desired fastening of the diaper about the waist of the wearer.

The present inventors have discovered that certain advantages are achieved by adding indicia to a disposable garment such as a diaper with the dual fastening system described herein. Indicia (32) may be included on various portions of the garment and may be configured in various shapes and areas to guide in fitting the garment. In the various embodiments, indicia (32) may comprise lines extending across front or rear waist region on the bodyfacing or garment facing surface (FIG. 3). In embodiments where the indicia (32) comprise lines, the lines generally extend at least about 1 inch, preferably at least about 4 inches, and most preferably from about 4 inches to about 6 inches across waist region (42, 44). Other shapes are contemplated. For example, indicia (32) may comprise alphanumeric characters (FIG. 2). The alphanumeric characters may indicate positions equidistance from the garments longitudinal centerline (66).

As used herein and in the claims that follow, the term "indicia" is meant to include any type of lines, patterns, ornamental designs, symbols, script, color codes, or other markings which have the capability, either inherently or with additional denotation, to aid an individual fitting the diaper to the wearer. Indicia may be perceptible using any of the senses.

Visual indicia may include paint, ink, dyes, or other coloring agents applied to, or visible through, a surface, as well as separate elements having indicia, such as a separate sheet of material secured to the surface, colored thread stitched or otherwise secured to the substrate to form the indicia, elastomeric elements having a different color than the substrate and secured thereto, or other elements having substantially the same function and effect, secured to the substrate. "Indicia" also includes luminescent material such as luminescent paint having luminescent pigments that radiate visible light when exposed to ultraviolet light. Examples of suitable luminescent paints are those made with phosphors, such as zinc or cadmium sulfides. Indicia also includes embossing or ultrasonic bonding. For example, embossing can darken the existing color of the material being embossed or provide a texture to the material being embossed. The embossing may reduce the bulk or softness of the material being embossed. Alternatively, in a two layer composite, embossing may allow the color of an underlying layer to become more visible through an upper layer.

Tactile indicia may include embossing, the addition of raised bumps to a surface or other elements which may be felt with the hands to aid an individual fitting the diaper to the wearer Indicia (32) preferably have bright colors so that the indicia are easily detected by a user. Indicia (32) preferably greatly contrast in color from the (typically white, light pink, or light blue) color of respective personal care articles. For example, in the embodiment of FIG. 3, the indicia (32) located on the bodyfacing surface of the rear waist regions comprise three elements. These elements can comprise blue, green and purple colors, respectively, or any other color combination. The element of the indicia (32) may be used to guide a user fitting the disposable garment regarding the positioning of the fasteners. The indicia (32) may guide the user regarding the lateral positioning of the fasteners. For example, the person installing the garment may utilize the multi-colored elements to insure that the fastening tabs (30) located in the waist regions opposite the indicia (32) are aligned an equal distance form the longitudinal centerline (66). Alternatively, the indicia (32) may guide the user regarding the longitudinal positioning of the fasteners. The person installing the garment may utilize the multi-colored elements to insure that the fastening tabs (30) located in the waist region opposite the indicia (32) are aligned an equal distance from the end edge (58). Alternatively, the indicia (32) may guide the user regarding the longitudinal and lateral positioning of the fasteners.

By placing the fastening tabs (30) at the proper longitudinal and lateral position increased comfort and better utilitarian operation are achieved. When the garment is placed on a wearer, and the front tabs are secured to the rear portion with the indicia (32) on the tab in alignment with indicia (32) on the waist region, the proper position is assured (as illustrated in FIG. 1).

FIG. 1 illustrates indicia located on the fastening tabs (30) located in the front waist region (42) as well as on the bodyfacing surface in the back waist region (44). The indicia located on the bodyfacing surface in the back waist region (44) comprise two sets of vertical lines. The innermost lines of the sets are equidistant from the longitudinal centerline (66). This provides the user an easy reference to place the right and left fastening tabs (30) equidistance from the longitudinal centerline (66). The indicia located on the fastening tabs (30) located in the front waist region (42) also comprise vertical lines. The vertical lines on the fastening tabs (30) may be used with the vertical lines on the bodyfacing surface in the back waist region (44) to further aid the user in placement of the fastener tabs (30). The indicia located on the fastening tabs (30) located in the front waist region (42) also comprise horizontal lines, which may be aligned with the end edge (58) or indicia located in the rear waist region (44) to insure that the front end edge (58) is aligned with the rear waist edge (58).

When a disposable garment contains a dual fastening system (80) compared to a single fastening system, this guide to positioning may be more important. With a single fastening system, the fasteners usually engage the garment facing surface of the front waist region (42). Realignment can be accomplished by repositioning one fastener in relationship to the other. However, in a dual fastening system, the fastener that engages the bodyfacing surface may not be visible. In addition, the four fasteners work together as a system; therefore, realizing that one fastener requires repositioning may require repositioning two, three or four fasteners. Therefore providing the user with a guide to position the fastener provides a useful benefit.

The fastener tabs (30) may comprises indicia (32) visible at, and optionally located on garment facing surface or the bodyfacing surface. The indicia (32) on the fastener tabs (30) may comprise first and second substantially parallel lines extending across substantially the entire length a fastening tab (30).

In placing a garment on a wearer, an installer utilizes the fastener tab (30) indicia (32) in combination with the indicia (32) located on the waist region opposite the fastener tab (30) as a guide, in fitting the personal care article to a wearer.

The indicia (32) may comprise any number of lines. The indicia (32) may comprise a plurality of longitudinally extending lines or a plurality of laterally extending lines, or a combination of longitudinally and laterally extending lines. The indicia (32) may be substantially symmetrically disposed about the longitudinal centerline (66).

Any of the indicia lines may be continuous or discontinuous (e.g. intermittent lines such as dashed lines, or lines of dots). Such discontinuities can apply, for example, to straight lines; and can apply equally well to, for example, curvilinear lines. Other types of indicia can be utilized. For example, the indicia can comprise jagged saw tooth type lines. The indicia may comprise sinusoidal type waves, or interactive shapes. Interactive shapes may include words that complete a phrase or a first shape located on one element and a corresponding or complementary shape located on a second element.

Any number of colors can be utilized in indicia (32). For example, in some embodiments, all of the lines can have the same color. However, preferably at least two different colors are present when there are at least two spaced parallel lines forming the indicia.

Embodiments wherein phosphors are utilized in constructing the indicia have numerous advantages. First, assuming a garment receives ambient light during the day, its indicia containing phosphors may be visible at night or in poor lighting.

Second, such garment will be easier to locate at night due to the luminescent effect of the indicia. Therefore, the garment will be easier to locate without operating a light and awakening other persons. Further, less light would be required for placement on a wearer at night. For example, a spent garment for an infant could be replaced with a fresh garment article having luminescing indicia. The amount of ambient light required to secure such fresh garment would be generally less than the amount of light required if such luminescing material were not available. Positioning of fastening tabs (30) would be relatively effortless because of using the luminescent indicia to assist in locating and securing fastening tabs (30).

Therefore, the garment could be changed with, minimal disturbance of the wearing infant or other adults, if present in the same room.

One of skill in the art will readily appreciate that the various first (82) and second (84) fasteners, first and second ears (90, 91) and positioning and type of indicia described herein may be combined to arrive at a number of configurations not illustrated herein, yet quite suitable for use in dual fastening systems.

Having described the invention in rather full detail, it will be readily apparent that various changes and modifications can be made without departing from the spirit of the invention. All of such changes and modifications are contemplated as being within the scope of the invention as defined by the appended claims and any equivalents thereto.

What is claimed is:

1. A disposable garment having opposed longitudinal side edges, opposed lateral end edges, a front waist region, a rear waist region and a crotch region which extends between and connects the front waist region and the rear waist region, the disposable garment comprising:
    a bodyfacing surface;
    a garment facing surface; and
    a dual fastening system, the dual fastening system comprising:
        at least two first fasteners located on first fastener tabs, at least a portion of each first fastener being situated inboard from each longitudinal side edge of the rear waist region, each first fastener being configured to engage at least a portion of the garment facing surface; and
        at least two second fasteners located on second fastener tabs, at least a portion of each second fastener being located in the front waist region and situated inboard from each longitudinal side edge of the front waist region, each second fastener being configured to engage at least a portion of the bodyfacing surface;
    wherein the bodyfacing surface comprises indicia in the rear waist region guiding a user fitting the disposable garment regarding the positioning of the second fasteners.

2. The disposable garment of claim 1 wherein the indicia in the rear waist region comprise first indicia, the second fastener tabs include second indicia, the second indicia cooperating with the first indicia in guiding a user regarding the positioning of the second fasteners.

3. The disposable garment of claim 1 wherein the indicia in the rear waist region guides the user fitting the disposable garment regarding the lateral positioning of the second fasteners.

4. The disposable garment of claim 1 wherein the indicia in the rear waist region guides the user fitting the disposable garment regarding the longitudinal positioning of the second fasteners.

5. The disposable garment of claim 1 wherein the indicia comprise visual indicia.

6. The disposable garment of claim 1 wherein the indicia comprise tactile indicia.

7. The disposable garment of claim 1 wherein the indicia comprise a plurality of longitudinally extending lines.

8. The disposable garment of claim 1 wherein the indicia comprise a plurality of laterally extending lines.

9. The disposable garment of claim 1 wherein the indicia comprise alphanumeric characters.

10. The disposable garment of claim 1 having a longitudinal centerline extending from the front waist region to the rear waist region, wherein the Indicia are substantially symmetrically disposed about the longitudinal centerline.

11. The disposable garment of claim 1 further comprising:
    an outer cover;
    a bodyside liner; and
    an absorbent core disposed between the bodyside liner and the outer cover.

12. The disposable garment of claim 1 wherein the first fastener and the second fastener are hook material.

13. A disposable garment having opposed longitudinal side edges, opposed lateral end edges, a front waist region, a rear waist region and a crotch region which extends between and connects the front waist region and the rear waist region, the disposable garment comprising:
    a bodyfacing surface:
    a garment facing surface; and
    a dual fastening system, the dual fastening system comprising:

at least two first fasteners located on first fastener tabs, at least a portion of each first fastener being situated inboard from each longitudinal side edge of the rear waist region, each first fastener being configured to engage at least a portion of the garment facing surface; and at least two second fasteners located on second fastener tabs, at least a portion of each second fastener being located in the front waist region and situated inboard from each longitudinal side edge of the front waist region, each second fastener being configured to engage at least a portion of the bodyfacing surface;

wherein the bodyfacing surface comprises first indicia in the rear waist region guiding a user fitting the disposable garment regarding the positioning of the second fasteners and the garment facing surface comprises indicia in the front waist region guiding a user fitting the disposable garment regarding the positioning of the first fasteners.

14. The disposable garment of claim 13 wherein the second fastener tabs include second indicia, the second indicia cooperating with the first indicia in guiding a user regarding the positioning of the second fasteners.

15. The disposable garment of claim 14 wherein the first fastener tabs include third indicia, the garment facing surface in the front waist region includes fourth indicia, the third Indicia cooperating with the fourth indicia in guiding the user regarding the positioning of the first fasteners.

16. The disposable garment of claim 13 wherein the first Indicia guides the user fitting the disposable garment regarding the lateral positioning of the second fasteners.

17. The disposable garment of claim 13 wherein the first indicia guides the user fitting the disposable garment regarding the longitudinal positioning of the second fasteners.

18. The disposable garment of claim 13 wherein at least a portion of the first indicia comprise visual indicia.

19. The disposable garment of claim 13 wherein at least a portion of the first indicia comprise tactile indicia.

20. The disposable garment of claim 13 wherein at least a portion of the first indicia comprise a plurality of longitudinally extending stripes.

21. The disposable garment of claim 13 wherein at least a portion of the first indicia comprise a plurality of laterally extending stripes.

22. The disposable garment of claim 13 wherein at least a portion of the first indicia comprise alphanumeric characters.

23. The disposable garment of claim 13 having a longitudinal centerline extending from the front waist region to the rear waist region, wherein the indicia are substantially symmetrically disposed about the longitudinal centerline.

24. The disposable garment of claim 13 further comprising:
an outer cover;
a bodyside liner; and
an absorbent core disposed between the bodyside liner and the outer cover.

25. The disposable garment of claim 13 wherein the first fastener and the second fastener are hook material.

26. A disposable absorbent article having opposed longitudinal side edges, opposed lateral end edges, a front waist region, a rear waist region and a crotch region which extends between and connects the front waist region and the rear waist region, the front waist region having a width extending between opposed longitudinal side edges and the rear waist region having a width extending between opposed longitudinal side edges, the disposable absorbent article comprising:

a garment facing surface comprising an outer cover;
a bodyfacing surface comprising a bodyside liner,
an absorbent core disposed between the bodyside liner and the outer cover; and
a dual fastening system, the dual fastening system comprising:
at least two first fasteners located on first fastener tabs, at least a portion of each first fastener being situated inboard from each longitudinal side edge of the rear waist region, each first fastener being configured to engage at least a portion of the garment facing surface; and at least two second fasteners located on second fastener tabs, at least a portion of each second fastener being located in the front waist region and situated inboard from each longitudinal side edge of the front waist region, each second fastener being configured to engage at least a portion of the bodyfacing surface;

wherein the bodyfacing surface comprises first indicia in the rear waist region guiding a user fitting the disposable absorbent article regarding the positioning of the second fasteners and the garment facing surface comprises indicia in the front waist region guiding a user fitting the disposable garment regarding the positioning of the first fasteners, and the first fastener and the second fastener are hook material.

* * * * *